US011596549B2

(12) United States Patent
Keller et al.

(10) Patent No.: US 11,596,549 B2
(45) Date of Patent: Mar. 7, 2023

(54) RING DESIGN FOR CAPSULOTOMY DEVICE

(71) Applicant: Centricity Vision, Inc., Fremont, CA (US)

(72) Inventors: Christopher Guild Keller, El Cerrito, CA (US); David Wong Manhin Sretavan, Tiburon, CA (US)

(73) Assignee: Centricity Vision, Inc., Carlsbad, CA (US)

( * ) Notice: Subject to any disclaimer, the term of this patent is extended or adjusted under 35 U.S.C. 154(b) by 355 days.

(21) Appl. No.: 16/945,121

(22) Filed: Jul. 31, 2020

(65) Prior Publication Data

US 2022/0031510 A1 Feb. 3, 2022

(51) Int. Cl.
*A61F 9/007* (2006.01)
(52) U.S. Cl.
CPC ........... *A61F 9/00754* (2013.01); *A61F 2230/0006* (2013.01)
(58) Field of Classification Search
CPC .............. A61F 9/00736; A61F 9/00754; A61F 9/00763; A61F 9/0079; A61F 2009/00887; A61F 2009/00889; A61F 2230/0004; A61F 2230/0006; A61F 2230/0008; A61B 18/082; A61B 18/085; A61B 18/14; A61B 2018/0019; A61B 2018/00196; A61B 2018/00601
See application file for complete search history.

(56) References Cited

U.S. PATENT DOCUMENTS

| | | | |
|---|---|---|---|
| 2011/0071524 A1* | 3/2011 | Keller | .................. A61F 9/0079 606/107 |
| 2014/0350554 A1* | 11/2014 | Keller | ................. A61F 9/00754 606/45 |
| 2017/0273733 A1 | 9/2017 | Weber | |
| 2018/0125711 A1* | 5/2018 | Keller | ................. A61F 9/00754 |
| 2019/0321092 A1 | 10/2019 | Keller | |

FOREIGN PATENT DOCUMENTS

WO    WO 2018/211507 A1    11/2018

OTHER PUBLICATIONS

PCT International Search Report and Written Opinion, PCT Application No. PCT/US2021/037133, dated Sep. 16, 2021, 13 pages.

* cited by examiner

*Primary Examiner* — Robert A Lynch
(74) *Attorney, Agent, or Firm* — Fenwick & West LLP (57) ABSTRACT

A device is described herein for performing capsulotomies that improves temperature uniformity and current flow around a cutting element of the device. The device includes a series of features whose geometries help remove cold and/or hot spots from the cutting element while maintaining the mechanical strength of the cutting element. In an embodiment, a device includes a cutting element and one or more electrical leads for providing an electrical discharge to the cutting element. The device further includes wire tabs configured to conductively couple an electrical lead to cutting element. Each wire tab includes a central conductive path and one or more conductive shunt paths conductively separated by one or more slots. The device further includes anchor tabs that are each associated with a slot disposed along the circumference of the cutting element and positioned to at least partially separate an anchor tab from a portion of the cutting element.

19 Claims, 9 Drawing Sheets

RING DESIGN FOR CAPSULOTOMY DEVICE

BACKGROUND

This description generally relates to medical devices and specifically to microsurgical instruments for capsulotomies.

Current tissue cutting devices often include a symmetric cutting ring for excising a portion of tissue. In theory, a purely symmetric conductive ring will have completely even electrical current flow with the same current density at all ring locations. However, in practice, conductive rings to perform actual tissue cutting are not isolated rings. The application of energy into the ring requires some method of attaching an external energy source to the ring. Likewise, current outflow from the ring will require a connection to an outside element. In addition, cutting rings are often attached to an additional superstructure via additional attachment features so that it can be easily handled and deployed. These attachment features disrupt the geometric symmetry of the ring and may lead to uneven current density and energy propagation at various ring locations, thereby compromising its intended tissue cutting function. This fundamental problem is accentuated if sequential micropulses of energy are delivered via the ring into tissues at fast speeds to achieve adequate tissue disruption while minimizing collateral tissue damage.

SUMMARY

Embodiments relate to a microsurgical device for tissue cutting that improves temperature uniformity and current flow around a cutting element of the device. The device includes a series of ring features whose geometries help prevent the formation of cold spots and/or hot spots resulting from structural asymmetries of the cutting element, such as various tabs of the cutting element. In addition, ring features help maintain the mechanical strength of the cutting element and provide a stronger physical attachment to a suction cup of the device due to improved tab configurations. Tabs may include one or more wire tabs, one or more mechanical tabs, and/or one or more anchor tabs. Ring features may include slots, cutouts, and/or bumps. Ring features can also be used to mitigate the formation of hot or cold spots in other situations where electrical current flow in a device is uneven due to any other type of spatial asymmetry in addition to the various types of tab structures discussed herein.

In an embodiment, a device includes a cutting element and one or more electrical leads for providing an electrical discharge to the cutting element. The device further includes one or more wire tabs protruding from the cutting element, each of the one or more wire tabs configured to conductively couple an electrical lead to the cutting element. Each wire tab includes a central conductive path and one or more conductive shunt paths conductively separated by one or more slots. The wire tabs may further include an additional slot disposed within the central conductive path of the wire tab that conductively separates portions of the central conductive path. The device further includes one or more anchor tabs protruding from the cutting element. The anchor tabs are each associated with a slot horizontally disposed along the circumference of the cutting element and positioned to at least partially thermally separate a respective anchor tab from a portion of the cutting element. In some embodiments, a first width of the cutting element includes a cutout adjacent to each of the one or more anchor tabs, where the first width of the cutting element is less wide than a second width of the cutting element.

The device may further include an anchor thread coupled to the cutting element via the one or more anchor tabs. The anchor thread is configured to compress the cutting element for insertion of the device through an incision. In some embodiments, the device further includes one or more mechanical tabs protruding from the cutting element. Each mechanical tab is adjacent to a slot horizontally disposed along the circumference of the cutting element and positioned to at least partially separate a respective mechanical tab from a portion of the cutting element. The device may also include a suction cup, where the cutting element is connected to the suction cup along a surface of the suction cup, such as an inner surface. In addition, the device may include a suction tube configured to provide suction to the suction cup. In these embodiments, the one or more electrical leads may be disposed within the suction tube. In some embodiments, the device further includes a rigid extender configured to compress the cutting element and/or a controller configured to control one or more electrical discharges to the cutting element. The controller may also be configured to control the amount of suction provided to the suction cup.

The figures depict various example embodiments of the present technology for purposes of illustration only. One skilled in the art will readily recognize from the following description that other alternative embodiments of the structures and methods illustrated herein may be employed without departing from the principles of the technology described herein.

DETAILED DESCRIPTION

Figure 1A:
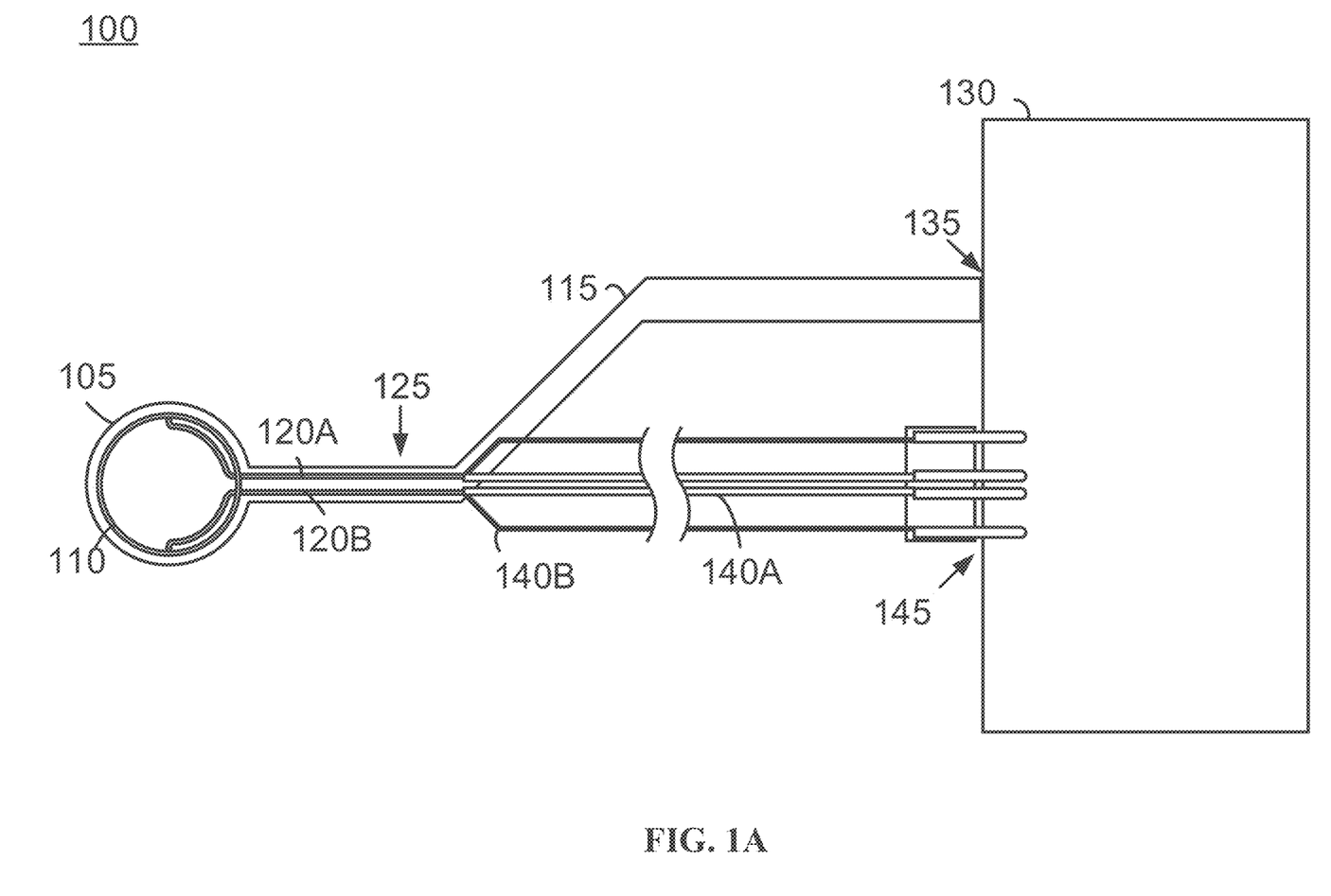
FIG. 1A illustrates a microsurgical device, according to one embodiment.
Figure 1B:
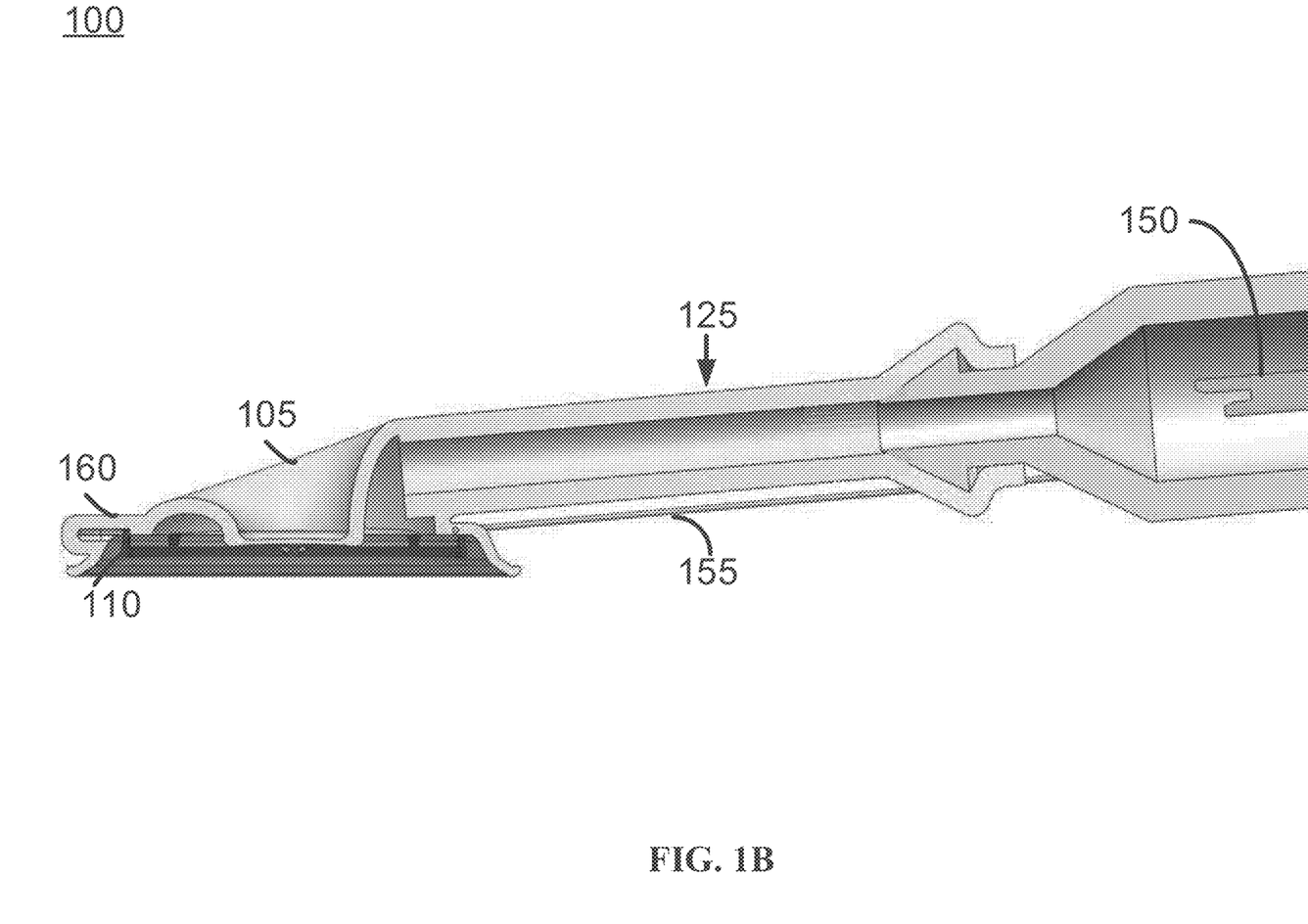
FIG. 1B illustrates a cross-sectional view of the microsurgical device shown in FIG. 1A, according to one embodiment.
Figure 1C:
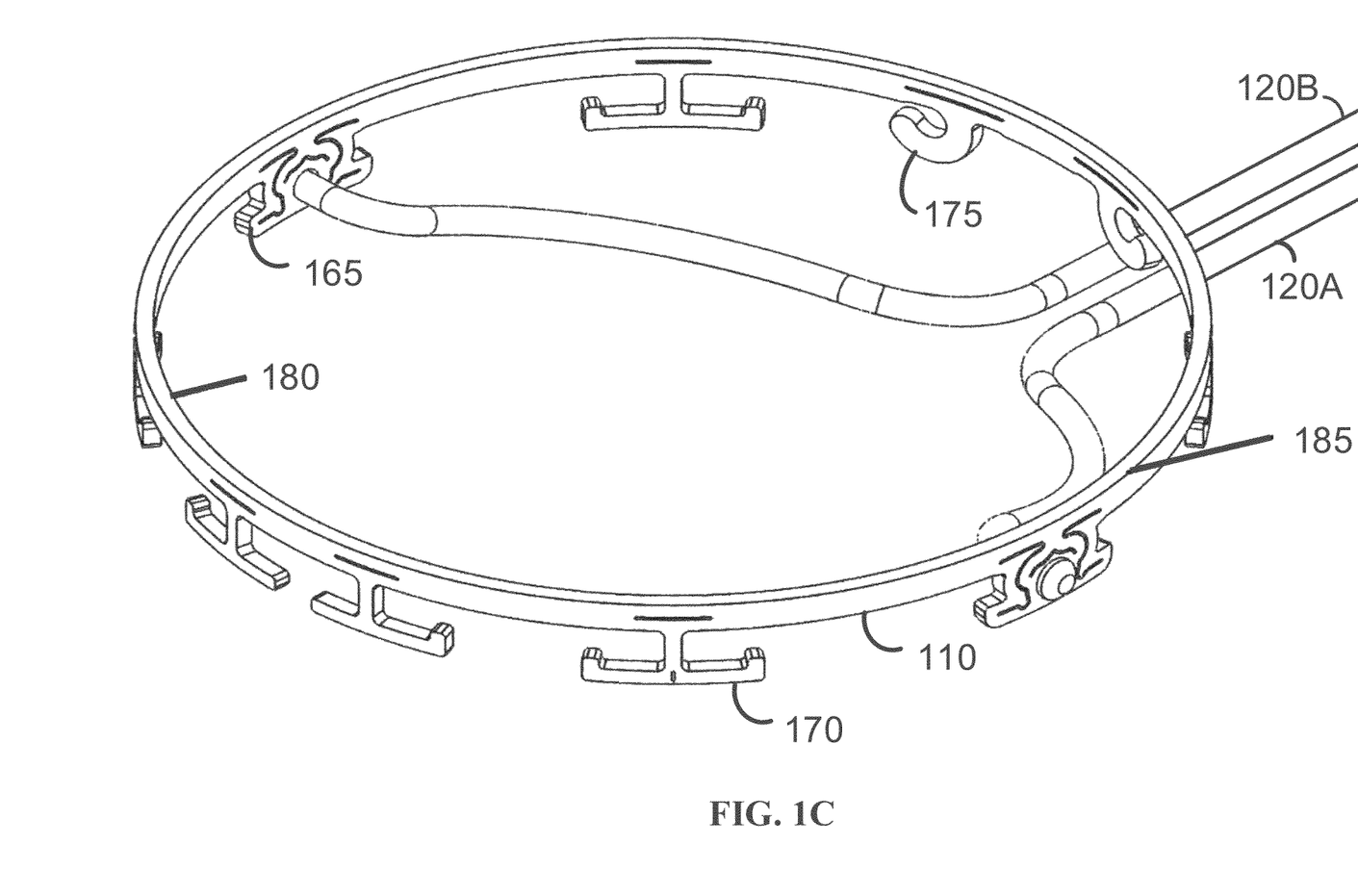
FIG. 1C illustrates a bottom perspective view of the cutting element of the microsurgical device shown in FIG. 1A, according to one embodiment.

Figures (FIGS.) 1A-1C illustrate various views of a microsurgical device 100 for tissue cutting. FIG. 1A illustrates an embodiment of a microsurgical device 100. FIG. 1B illustrates a cross-sectional view of the microsurgical device 100. FIG. 1C illustrates a bottom perspective view of the cutting element of the microsurgical device 100.

The device 100 shown in FIG. 1A includes a suction cup 105, a cutting element 110 (also referred to as "cutting ring"

herein), one or more suction tubes 115, electrical leads 120A, 120B, and a stem 125. The suction cup 105 and cutting element 110 are located at a distal end of the stem 125, which houses the one or more suction tubes 115 and the electrical leads 120A, 120B. The device 100 further includes a control console 130 (also referred to as "controller" herein) that is configured to provide suction to the suction cup 105 and electrical energy to the cutting element 110. The suction cup 105 is connected to the control console 130 via the one or more suction tubes 115 and a suction connector 135. The cutting element 110 is connected to the control console 130 via the electrical leads 120A, 120B, one or more sets of electrical conductors, such as electrical conductors 140A, 140B, and an electrical connector 145.

The suction cup 105 is a foldable structure that can provide a water-tight seal between the edges of the suction cup 105 and the tissue being excised (e.g., lens capsule, corneal tissue, connective tissue, and the like). Because of the fluidic seal between the suction cup 105 and the tissue, vacuum pressure can be applied to the suction cup 105 and the tissue so that the resulting pressure presses the cutting element 110 against the tissue. Pressing the cutting element 110 against the tissue facilitates a more precise, smoother cut. The foldable structure of the suction cup 105 is reversibly collapsible such that a cross-section of the suction cup 105 can decrease for insertion of the device 100 through an incision. As such, the suction cup 105 may include a compliant material, such as silicone, polyurethane, and the like.

The cutting element 110 is an element designed to cut tissue through application of pressure and/or electrical current via one or more electrical leads 120A, 120B coupled to the cutting element 110. The cutting element 110 can be made from various materials. In some embodiments, the metallic components of the cutting element 110 may be made by electroforming suitable materials such as nickel, nickel-titanium alloys, gold, steel, copper, platinum, iridium, molybdenum, tantalum, and the like. When the cutting element 110 is configured to electrically excise tissue, the material for the cutting element 110 is electrically conductive. In addition, the cutting element 110 is reversibly collapsible such that a cross-section of the cutting element 110 can decrease for insertion of the device 100 through an incision. Therefore, the material of the cutting element 110 is generally elastic so that it can return to its original shape after insertion of the device 100 through the incision. A typical construction example is a superelastic nitinol ring having a wall thickness of 0.075 mm, height of 0.140 mm, and tabs as described in this specification. Another strategy is to add to this superelastic body a thin film (e.g., 0.0001 to 0.002 mm) of a more conductive material that does not have to be superelastic because it is very thin. Examples of materials include, but are not limited to, spring steel, stainless steel, titanium nickel alloy, graphite, nitinol, nickel, nickel-chrome alloy, tungsten, molybdenum, tantalum, gold, silver, or any other material that will allow the cutting element 110 to return to its prior shape.

The device 100 is capable of delivering a wide range of energies (e.g., from 0 to 3 joules, or more) via the cutting element 110. The energy dissipated by the cutting element 110 during use in surgery may be determined empirically through use on a specific tissue of interest. For example, in a capsulotomy of the anterior lens capsule of an adult human, it was found that about 1.2 joules produce a satisfactory result. Some specific example of applications to lens capsulotomies include pediatric, adult, and dog, listed in order of increasing energy need. To accommodate the varying energy needs, the amount of energy dissipated by the cutting element 110 may be controlled by controlling parameters such as the number of pulses, duration of each pulse, time between pulses, and/or energy of each pulse applied to the tissue via the cutting element 110. These parameters may be determined empirically for each tissue application and/or via computational modeling. In addition, temperature gradients in the cutting element 110 may be designed and/or modified for different tissues.

It is helpful to have a uniform wall thickness over the entire circumference of the cutting element 110 to maintain the correct current density and heating everywhere along the cutting element 110. The standard methods of drawing nitinol tubing may result in excessive variation in wall thickness. In areas that are thicker, the temperature will be too low, and a relative cold spot may occur. In areas that are too thin, a relative hot spot may occur. One method of making a uniform wall thickness is to build up the nitinol tubing by sputtering nitinol onto a rotating mandrel in a vacuum chamber.

Another method to make a uniform wall thickness is to take drawn nitinol tubing with a nominal wall thickness greater than the desired final wall thickness of the cutting element 110, cut the tubing into short lengths (e.g., 25 mm). Bring the inner diameter to the correct dimension and roundness by using common machining methods such as honing, ID grinding, lapping, and polishing. Cool it to transform it into low stiffness martensite, and force the piece onto a slightly oversized precision round support shaft to force the inner diameter to be round. Or instead, heat the nitinol to increase its diameter (e.g., heat to 400 C) so it can be slid without force over the cold mandrel. Then the outer diameter can be precision ground, lapped, and/or polished to also be round, concentric to the inner diameter and have the desired final wall thickness. The outer surface of the support shaft is a material that can be etched away without affecting nitinol or the body of the shaft. For example, the support shaft may be solid, or tubular 316 stainless steel, with a thin layer (e.g., 0.02 mm) of copper plated or sputtered on it. Other materials that can be etched away without harming the nitinol or mandrel can be used (copper is easy as it can be quickly removed with nitric acid, and nitric acid passivates nitinol). After the nitinol is machined to have uniform wall thickness, the support shaft is mounted onto a femtosecond laser cutting system that supports both ends of the shaft on frictionless air bearings such that it can be precisely rotated and translated by computer-controlled actuators. A side view pattern can then be cut into the tube. The laser beam does not fully penetrate the etchable layer, so the support shaft remains undamaged and can be reused. The cutting element 110 slides off the shaft after the etchable layer is etched away. Another option in construction is that after the sacrificial etchable layer is deposited, one or more layers of other materials may be deposited prior to mounting the nitinol on the mandrel. For example, a precision mandrel of 316 stainless steel may have a layer of copper deposited (e.g., 0.02 mm), and on top of the copper, a layer of molybdenum could be deposited (e.g., 0.001 mm), and then a layer of tantalum (e.g., 0.0001 mm). One way to deposit these layers is by sputtering on the mandrel spinning about its long axis. Another method is by electroplating. The laser cutting beam stops in the Cu layer, so the NiTi, Ta, and Mo layers are all cut through. After etching away the Cu, the Mo/Ta layers are held by compressive force in the nitinol ring (since the NiTi was heated to slide over the mandrel, and then shrunk down when cool). The Mo layer will carry 15 times more current than the same thickness of NiTi, so it allows more of the power to be dissipated at the ID of the cutting edge, and the wall thickness of the NiTi can be decreased which enables it to be bent to a smaller radius as needed to enter a smaller incision in tissue.

The one or more suction tubes 115 are located within the stem 125 of the device 100. The one or more suction tubes 115 are configured to provide suction to the suction cup 105. The one or more suction tubes 115 provide suction to the suction cup 105 to compress the suction cup 105 against the tissue being excised. The one or more suction tubes 115 may also be configured to reverse the suction fluid flow being applied to the suction cup 105 to disengage the suction cup 105 and cutting element 110 from the excised tissue.

The one or more suction tubes 115 may be further configured to act as fluid paths. For example, the one or more suction tubes 115 may be primed before use with a solution, such as a balanced salt solution. Priming the fluid paths of the one or more suction tubes 115 helps ensure that there is little to no compressible air in the device 100. In addition, after excision of the tissue is complete, a hydraulic release of the one or more suction tubes 115 may be performed to release the suction cup 105 from the tissue. In some embodiments, the hydraulic release consists of forcing 0.05 ml to 0.2 ml of a balanced salt solution from the suction tubes 115 back into the suction cup 105.

The configuration of the suction tubes 115 along the inner surface of the suction cup 105 may vary. For example, when there are two or more suction tubes 115, the suction tubes 115 may be located at antipodal points of the suction cup 105. This configuration may ensure equal distribution of suction throughout the suction channel of the suction cup 105. In other embodiments, the suction tubes 115 may be adjacent, located within a threshold number of degrees of each other, located within a threshold distance of each other, and the like. Further, the suction tubes 115 may be located along an outer surface of the suction cup 105, along a bottom surface of the suction cup 105, along a top surface of the suction cup 105, and the like. In embodiments where the device 100 includes a single suction tube 115, the suction tube may be located at any point along the inner surface of the suction cup 105. For example, an orifice of the suction tube 115 may be located in a roof of the suction cup 105, at a proximal end of the suction cup 105, at a distal end of the suction cup 105, and the like.

The electrical leads 120A, 120B are configured to provide electrical energy to the cutting element 110. The electrical leads 120A, 120B are located within the stem 125 of the device 100 and coupled to a surface of the cutting element 110. In some embodiments, the electrical leads 120A, 120B are silver wires. In other embodiments, the electrical leads 120A, 120B are made of copper, aluminum, gold, or the like. In addition, the electrical leads 120A, 120B may insulated.

The control console 130 is configured to provide suction to the suction cup 105 and electrical energy to the cutting element 110. In addition, an operator of the device 100 may control the depth of cut via the control console 130 by modifying the suction and/or electrical parameters of the device 100.

Suction is provided to the suction cup 105 via one or more suction tubes 115 connected to the control console 130 and a suction connector 135. Using the control console 130, an operator of the device 100 may provide suction to the suction cup 105, reverse suction during disengagement of the device 100, and/or flush the fluid paths of the one or more suction tubes 115 with a solution. In addition, an operator of the device 100 may modify the amount of suction applied to the suction cup 105 based on the operation being performed. In some embodiments, an operator of the device 100 may manually modify the amount of suction applied to the suction cup 105, for example using a vacuum valve and a vacuum gauge of the control console 130. Alternatively, or additionally, the control console 130 may include predetermined suction parameters determined via experimentation, modeling, and/or a combination thereof that are each associated with a procedure. In addition, using the control console 130, different amounts of suction may be provided to different suction tubes. By way of example, suction pressure of 19+/−1 inch of Hg vacuum has been used successfully. That is gauge pressure, not absolute pressure, so the same pressure differential is established by the console across the suction cup wall regardless of altitude at which it is used.

The control console 130 delivers electrical energy to the cutting element 110 via the electrical leads 120A, 120B, one or more sets of electrical conductors 140A, 140B, and an electrical connector 145. A first set of electrical conductors 140A may be configured to provide power to the cutting element 110. A second set of electrical conductors 140B may be for resistance measurement and may be connected to a measurement device, such as a Kelvin probe (also known as the 4-wire resistance measurement method). In some embodiments, the first set of electrical conductors 140A and/or the second set of electrical conductors 140B are copper wires, such as (respectively) 24 ga copper wires, 30 ga copper wires, and the like. In other embodiments, the first set of electrical conductors 140A and/or the second set of electrical conductors 140B are composed of aluminum, gold, silver, or the like. Electrical energy may be provided to the cutting element 110 as one or more electrical waveforms. The one or more electrical waveforms are discharged through the cutting element 110 to cause the cutting element 110 to heat up for a short time, such as 0.0001 seconds to 0.05 seconds, depending on the applied voltage and current.

Using the control console 130, the depth of cut may be controlled by controlling the amount of electrical discharge applied to the cutting element 110. For example, the depth of cut may be controlled by modifying one or more of: the energy of each pulse, the number of pulses in the pulse train, the inter-pulse intervals, and the like. As with the suction, these parameters may be manually modified by an operator of the device 100 using control elements of the control console 130. Alternatively, or additionally, the control console 130 may include predetermined sets of parameters that are each associated with different depths of cut, different patient types, and the like. These sets of parameters may be determined through experimentation, modeling, and/or a combination thereof. The control console 130 may be a controller, microprocessor, a programmable hardware logic, etc.

In some embodiments, the control console 130 may change the operating parameters of the device 100 automatically. For example, the control console 130 may change the operating parameters according to a predetermined set of operating steps associated with a procedure. Alternatively, or additionally, the control console 130 may change the operating parameters of the device 100 based on feedback from the device 100 itself. For example, the control console 130 may change the operating parameters of the device 100 in response to a detection of a pressure, a pressure change, a temperature, a temperature change, a determined depth of cut, or the like, during use.

FIG. 1B illustrates a cross-sectional view of the microsurgical device 100. As shown, the cutting element 110 is coupled to an inner surface of the suction cup 105 for excising a portion of the tissue abutting the outer surface of the suction cup 105 and/or cutting element 110. In alternative configurations, the cutting element 110 may be coupled to an outer surface of the suction cup 105, along a bottom surface of the suction cup 105, along a top surface of the suction cup 105, or the like.

In the embodiment shown, the device 100 includes a rigid extender 150 and an anchor thread 155. The rigid extender 150 is retractable and used to reversibly compress the suction cup 105 and cutting element 110 for insertion of the device 100 through an incision, such as an incision of a lens capsule. To insert the device 100 into the eye, the rigid extender 150 stretches the suction cup 105 and cutting element 110 in one direction while the anchor thread 155 stretches the suction cup 105 and cutting element 110 in the opposite direction. This reversibly straightens out and decreases the cross-section of the suction cup 105 and cutting element 110 so that the suction cup 105 and cutting element 110 can go through the incision. Examples of incision sizes commonly used in surgery include 1.8 mm, 2.0 mm, 2.2 mm, 2.4 mm, etc.) As the rigid extender 150 is removed from the eye, the suction cup 105 and cutting element 110 elastically return to their original shape. The rigid extender may also be used to straighten the device after tissue cutting to facilitate device removal from the eye. There may be sufficient slack in the anchor thread 155 so that the cutting element 110 is not constrained except during extension of the rigid extender 150 and removal of the device 100 from the eye. The anchor thread 155 may be made from Vectran, a fiber that can withstand high temperature. In some embodiments, the device 100 includes a pocket 160 to house the rigid extender 150 once extended. In some embodiments, the device 100 does not include a rigid extender 150 anchor thread 155, and/or pocket 160.

FIG. 1C illustrates a bottom perspective view of the cutting element 110 of the microsurgical device 100. The bottom of the cutting element 110 is continuous such that current can flow around the bottom of the cutting element 110 in a continuous path and generate the heat necessary for excising tissue. The cutting element 110 includes tabs, such as tabs 165, 170, 175, that are configured to couple the electrical leads 120A, 120B to the cutting element 110, couple the suction cup 105 to the cutting element 110, and/or couple an anchor thread 155 to the cutting element 110. The cutting element 110 and/or tabs may include features, such as slots, cutouts, and bumps, to remove hot and/or cold spots and maintain the mechanical strength of the cutting element 110. The design and functionality of the tabs and features are discussed in detail below with reference to FIGS. 3A-6.

The cutting element 110 may be configured so that it lies perpendicular to the surface of the tissue being excised. For example, the cutting element 110 shown in FIG. 1C is cylindrical such that the cutting element 110 is substantially perpendicular to the portion of the tissue being excised. In addition, the cutting element 110 may be configured such that only an inner corner edge 180 of the cutting element 110 excises the tissue. Alternatively, the cutting element 110 may be configured such that only the outer corner edge 185 of the cutting element 110 excises the tissue, both the inner corner edge 180 and outer corner edge 185 of the cutting element 110 excise the tissue, or the like. In addition, the cutting element 110 may be elliptical, conical, linear, square, rectangular, triangular, or any other suitable shape to match the geometry of the tissue being excised.

The device 100 shown includes two electrical leads 120A, 120B. Alternatively, the device 100 may include greater or fewer electrical leads, such as one electrical lead, three electrical leads, four electrical leads, etc. The points at which the electrical leads 120A, 120B couple to the cutting element 110 may vary. For example, when the electrical leads 120A, 120B are positioned on opposite sides of the cutting element 110, the current can travel in opposite directions to conduct current uniformly around the portion of the tissue being excised. Alternatively, the electrical leads 120A, 120B may be located at positions that are a threshold distance apart, a threshold number of degrees apart, or the like.

The electrical leads 120A, 120B may be located within the one or more suction tubes 115. In other embodiments, the electrical leads 120A, 120B may be located outside of the one or more suction tubes 115. For example, the electrical leads 120A, 120B may be coupled to an outer surface of the one or more suction tubes 115, adjacent to the one or more suction tubes 115, and/or separated by a threshold distance from the one or more suction tubes 115, etc.

Figure 2:
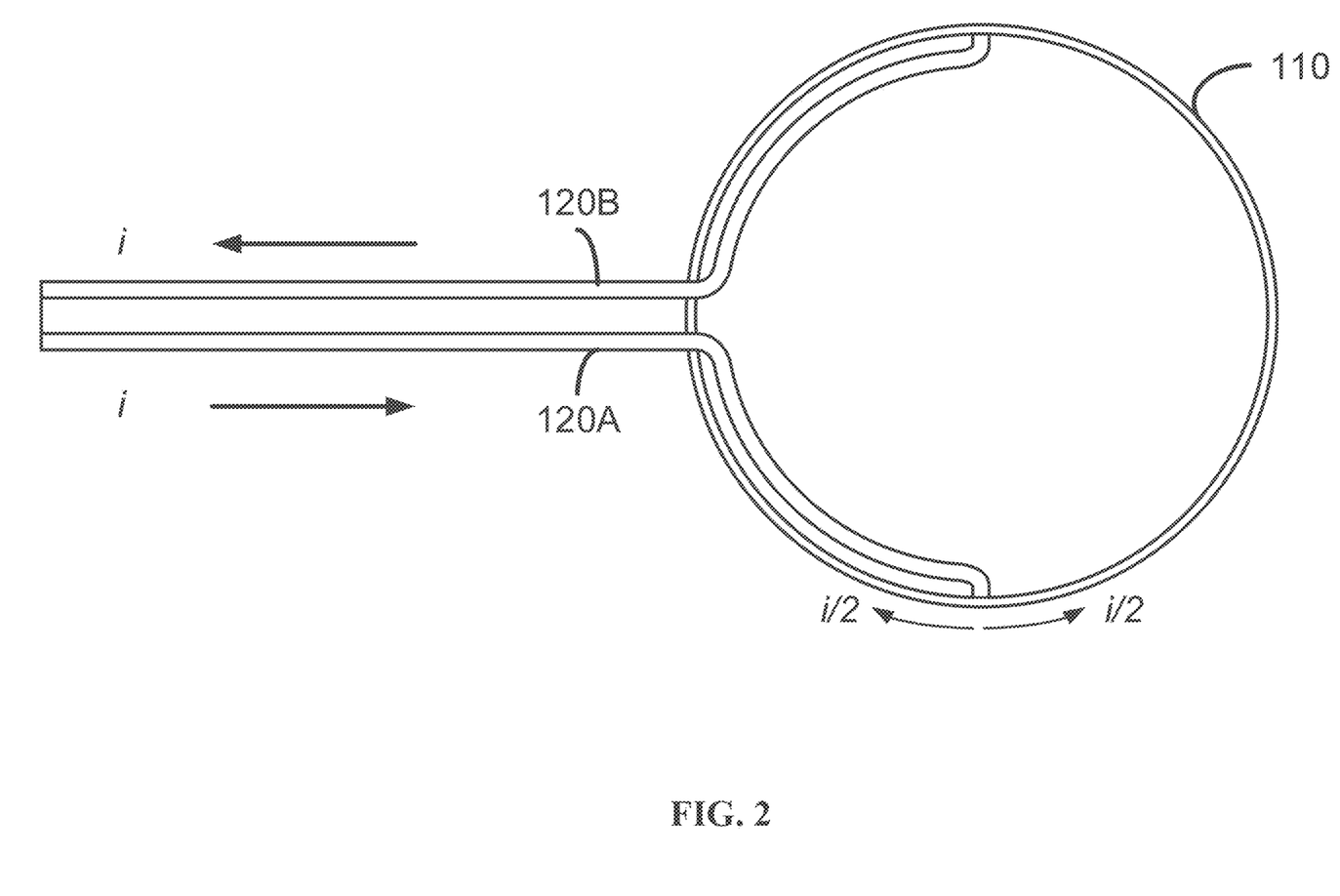
FIG. 2 illustrates the flow of current through the cutting element of the microsurgical device shown in FIG. 1A, according to one embodiment.

FIG. 2 illustrates the path of electrical current flow (i) within the cutting element 110. Upon entering the cutting element 110 through an electrical lead 120A, a portion of the current, such as one half of the current ($i_{1/2}$), travels along one half of the cutting element 110, while another portion of the current, such as the other half of the current ($i_{1/2}$), travels along the other half of the cutting element 110. Current then exits the cutting element 110 at the other electrical lead 120B. Due to the electrical resistance of the cutting element 110, the current flow causes a rapid increase in the temperature of the cutting element 110. Because of the rapid increase in temperature, the water molecules near or adjacent to the cutting element 110 and the tissue being excised vaporize rapidly and mechanically fracture the tissue along the path dictated by the portion of the cutting element 110 abutting the tissue being excised.

Tab and Feature Design

As shown in FIG. 1C, tabs of various tab types protrude from the cutting element 110. Tab types include, but are not limited to wire tabs, such as wire tab 165, mechanical tabs, such as mechanical tab 170, and anchor tabs, such as anchor tab 175. In some embodiments, wire tabs conductively couple the electrical leads 120A, 120B to the cutting element 110, mechanical tabs hold the cutting element 110 within the suction cup 105, and anchor tabs couple the cutting element 110 to an anchor thread 155. The size, shape, and position of each tab type varies because of their different functions, which introduces structural asymmetries to the cutting element 110.

The problem of uneven current flow and temperature elevation in the cutting element 110 due to the required structural asymmetries may be solved by adding an intricate pattern of one or more features to the cutting element 110 and/or tabs protruding from the cutting element 110. Features may include a combination of slots, cutouts, and/or bumps. The configuration and geometry of the features also maintain the mechanical strength of the cutting element 110. Mechanical strength is maintained by ensuring that the features do not create mechanically weak regions in the cutting element 110 or create hot spots that can become mechanically weak areas after energy pulses have been applied to the cutting element 110.

Figure 3A:
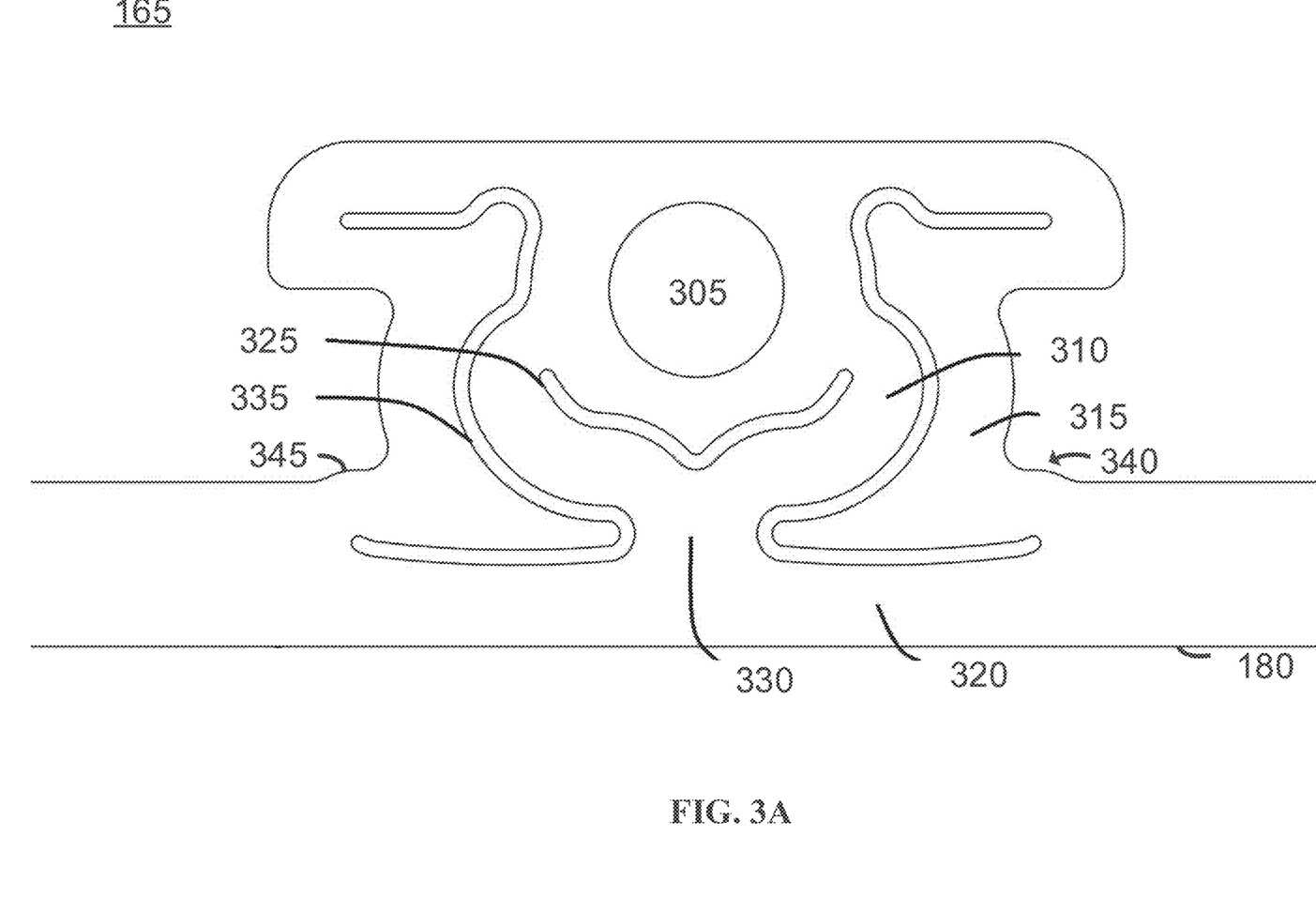
FIG. 3A illustrates a wire tab of the microsurgical device shown in FIG. 1A, according to one embodiment.

Slots, such as slot 325 in FIG. 3A, function as empty space devoid of conductive material to provide electrical insulation. For example, slots stop current flow and divert current flow into an alternative path in the cutting element 110. In addition, as regions devoid of conductive material, the slots also provide thermal insulation by eliminating the heat conductive path. Introduction of slots into the cutting element 110 and/or tabs protruding from the cutting element 110 may be of any size or shape, such as slots 325, 335 in FIG. 3A. The cutting of the slots can be a closed path area, or single pass line. For example, slots may be made by one pass of the laser. In some embodiments, the slot width is around 0.013 mm. In some embodiments, instead of an empty space devoid of conductive material, slots may be made of a non-conductive material.

Figure 5:
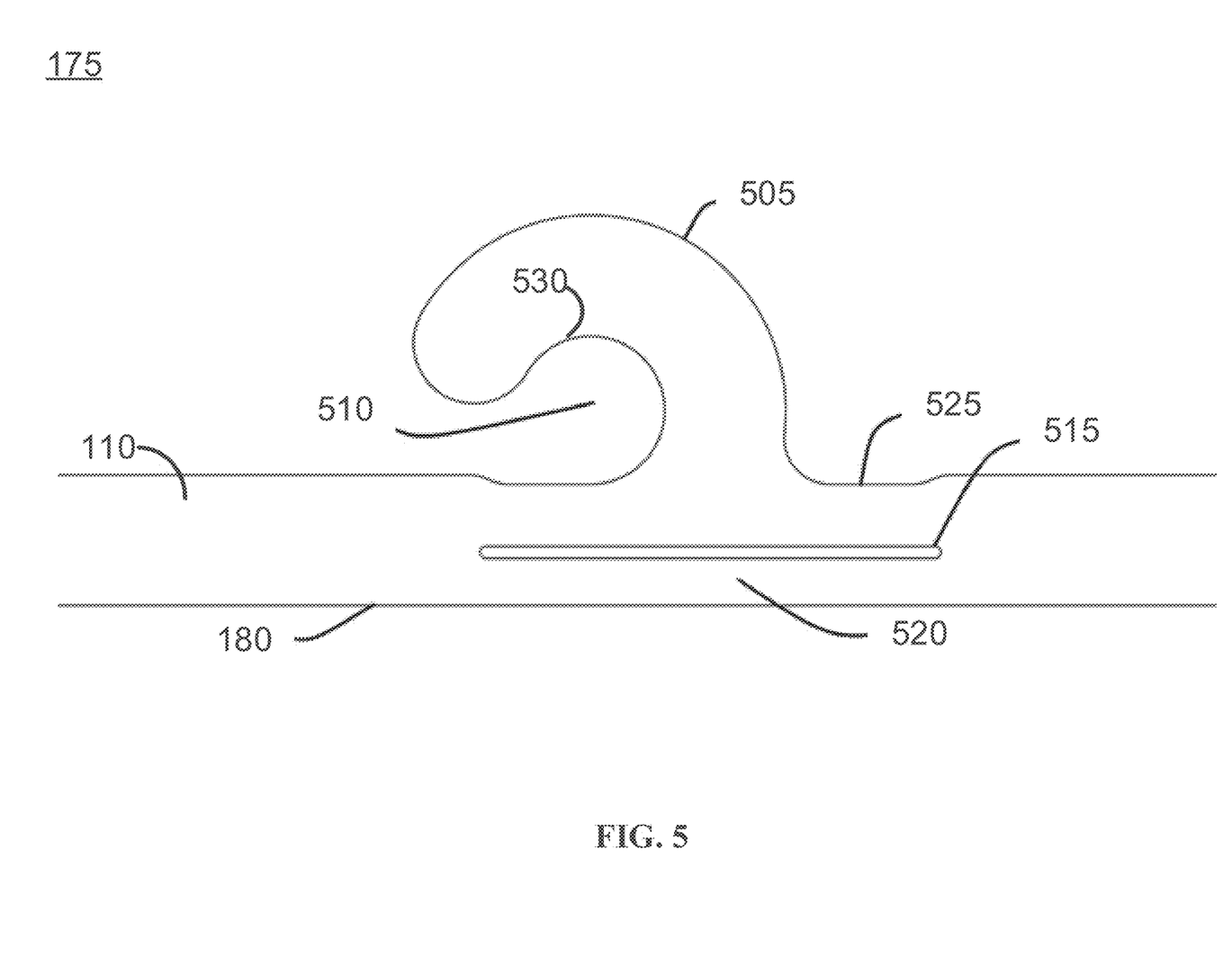
FIG. 5 illustrates an anchor tab of the microsurgical device shown in FIG. 1A, according to one embodiment.

Cutouts, such as cutout 525 in FIG. 5, reduce the cross-section of the cutting element 110 at various loci along an edge of the cutting element 110 to reduce the amount of material at the various loci. Reducing the amount of material locally increases the current density and provides appropriate heating at specific locations along the cutting element 110. For example, cutouts may be used to offset cold spots caused by anchor tabs and/or mechanical tabs.

Conductive material is added to various portions of the cutting element 110 in the form of bumps to accommodate nearby regions of undesired high current density. For example, bumps, such as bump 345 in FIG. 3A, may be used to counteract hot spots that secondarily form through the implementation of slots in other portions of the cutting element 110. Hot spots may potentially translate in mechanically weak regions after use.

The geometry and configuration of features along the cutting element 110 may be based on the tab type the feature is associated with, the position of the feature, the proximity of the feature to the electrical leads 120A, 120B, the proximity of the feature to the suction cup 105, and the like. For example, mechanical tabs and/or anchor tabs may have horizontal slots cut in the cutting element 110 under the tabs, and wire tabs may have vertical or bent slots disposed within the tab itself. A horizontal slot allows the electrical current to flow horizontally around the cutting element 110, but blocks thermal conduction vertically from the inner corner edge 180 of the cutting element 110 to the cold tab. A vertical or bent slot may help distribute and/or divert electrical current across various paths of the tab.

The geometry and configuration of each feature may be determined via reiterative empirical testing of their combined effects on current flow and temperature elevation in the cutting element 110. Reiterative empirical testing is particularly relevant for conductive materials, such as shape memory alloys (e.g. nitinol) whose electrical resistance change as a function of temperature since the material's resistance and temperature simultaneously change during use. In addition, because thermal transport out of the cutting element 110 changes as adjacent water turns to steam, and because the specific heat capacity and thermal conductivities rapidly change as functions of temperature and pressure, reiterative empirical testing may be used to fine tune feature details, such as size, geometry, and/or curvature, without having to explicitly quantify changes in thermal transport over short timeframes (0.0001 seconds to 0.05 seconds). Therefore, reiterative empirical testing may be used to ensure even current flow and energy delivery via the cutting element 110 into tissue during an entire multi-pulse procedure. Alternatively, or additionally, computation modeling may be used to determine the geometry and configuration of each feature.

FIG. 3A illustrates a wire tab 165 of the microsurgical device 100 shown in FIG. 1A. Wire tabs conductively couple the electrical leads 120A, 120B to the cutting element 110. To conductively couple an electrical lead to the cutting element 110, an electrical lead, such as electrical lead 120A or electrical lead 120B, is inserted through a lumen 305 of the wire tab 165. Once inserted, the end of the electrical lead protruding from the lumen 305 may be formed into a rivet head to secure the electrical lead to the wire tab 165. In some embodiments, the electrical leads 120A, 120B are made of a material that is easily plastically deformed, such as silver. As such, compressive stress on each electrical lead causes the electrical lead to expand within the lumen 305, which ensures sufficient physical contact and electrical connection between the electrical lead and the cutting element 110. In some embodiments, the diameter of the lumen 305 is around 0.150 mm, and the diameter of the wire is around 0.127 mm.

The wire tab 165 includes multiple conductive paths to carry the electrical current from the electrical lead, such as electrical lead 120A or electrical lead 120B, to the cutting element 110. The multiple conductive paths ensure that the proper current density is provided to the inner corner edge 180 of the cutting element 110 and eliminate a potential cold spot from forming at the portion of the cutting element 110 directly underneath the wire tab 165. As shown in FIG. 3A, the wire tab 165 includes central conductive paths 310 and a conductive shunt path 315 on either side of the central conductive paths 310. Current is carried by the central conductive paths 310 to the bottom beams 320. However, the bottom beams 320 may be too small to carry the entire current, so the conductive shunt paths 315 may carry the rest of the current to cutting element 110 including the inner corner edge 180. In some embodiments, the conductive shunt paths 315 may carry up to or greater than 12% more current than the central conductive paths 310.

The wire tab 165 shown includes a wire tab slot 325 that electrically and thermally insulates the sides of the central conductive path 310 from the electrical lead. The wire tab slot 325 helps to limit downward current flow to the neck 330 of the wire tab 165 and causes an appropriate current to flow along the conductive shunt paths 315. The wire tab 165 shown also includes a wire tab slot 335 that electrically and thermally insulates the sides of the central conductive path 310 and the bottom beams 320 from the conductive shunt paths 315. The wire tab slot 335 also directs current away from the neck 330 of the wire tab 165, eliminating a hot spot from forming in the cutting element 110 under the wire tab 165. In some embodiments, the wire tab 165 and the cutting element 110 are continuous and/or made out of the same material.

As a result of the thermal stresses placed on the cutting element 110 during use, the mechanical forces applied to the cutting element 110 during device 100 removal may cause the cutting element 110 to break. To minimize stress concentrations in the cutting element 110 and maintain its mechanical strength, the end of the wire tab slot 335 has a slight upward curve, which removes concentrations of stress in the metal of the cutting element 110. The upward curve of the wire tab slot 335 may cause increased current density along the top half of the cutting element 110, particularly at point 340, which is directly above the curved end of the wire tab slot 335. To offset the increased current density, the cutting element 110 may include bumps, such as bump 345, on either side of the wire tab 165. A bump increases the amount of material at point 340, and, therefore, reduces the local current density of the cutting element 110 at point 340. As shown, a similar bump may be placed on the opposite side of the wire tab 165.

Figure 3B:
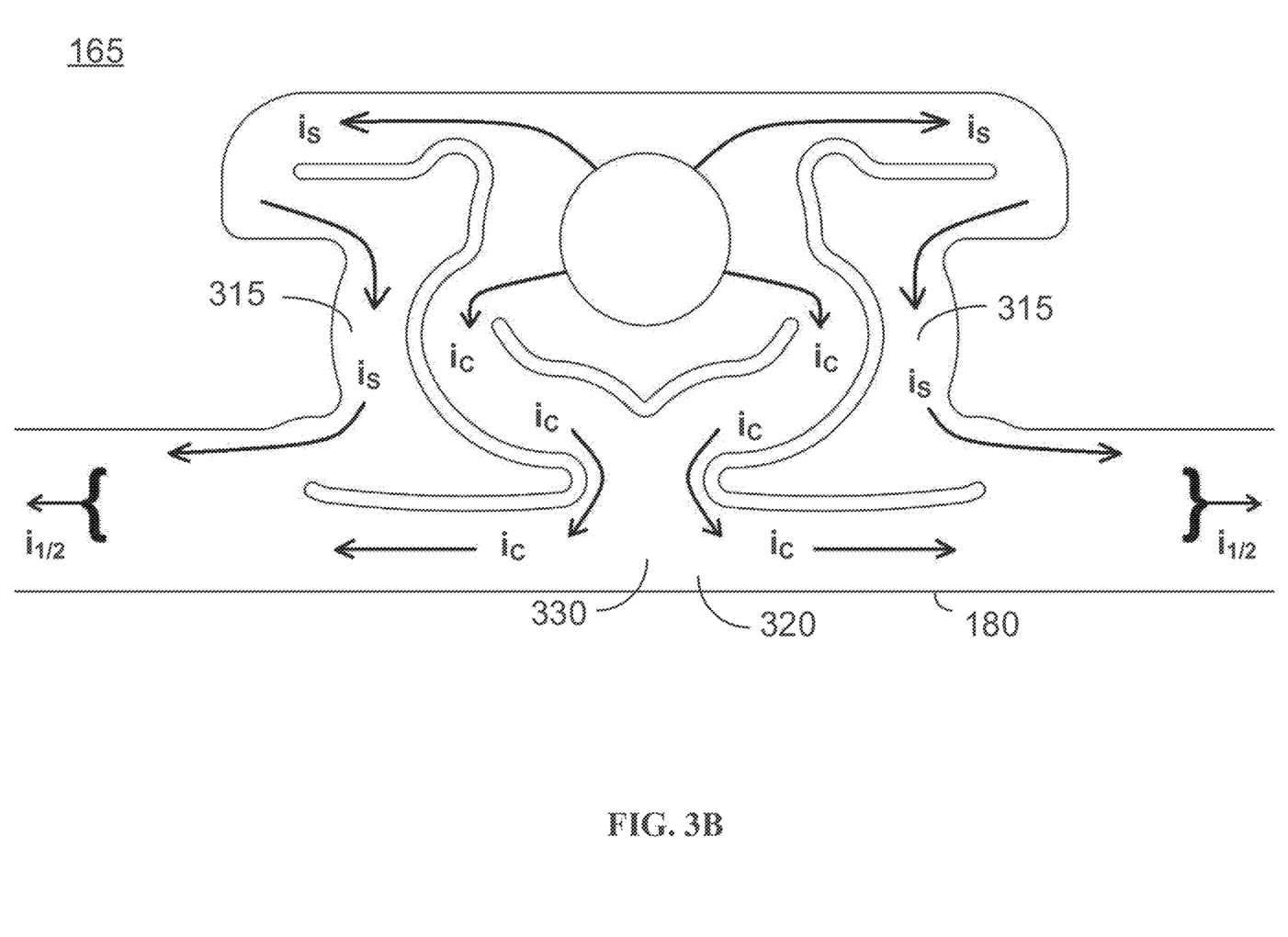
FIG. 3B illustrates the flow of current through the wire tab shown in FIG. 3A, according to one embodiment.

FIG. 3B illustrates the flow of current through the wire tab 165 shown in FIG. 3A. The total current $i_{total}$ carried by an electrical lead, such as electrical lead 120A or electrical lead 120B, is distributed through the wire tab 165 according to Equation 1.

$$i_{total} = 2(i_c + i_s) \tag{1}$$

In Equation 1, $i_c$ is the current carried by each central conductive path 310 and $i_s$ is the current carried by each conductive shunt path 315. The electrical current $i_c$ carried by each of the central conductive paths 310 converges at the neck 330 of the wire tab 165 and is carried along the bottom beams 320 along the path shown. Heat from the neck 330 and adjacent bottom beams 320 prevents any significant cold spot from occurring underneath the wire tab 165.

The electrical current $i_s$ carried by each of the conductive shunt paths 315 travels to the top half of the cutting element 110 along the path shown. The electrical current $i_s$ carried by a conductive shunt path 315 converges with the electrical current $i_c$ carried by one of the central conductive paths 310. As a result, a first half of the total current $i_{1/2}$ goes clockwise and a second half of the total current $i_{1/2}$ goes counterclockwise.

Figure 4:
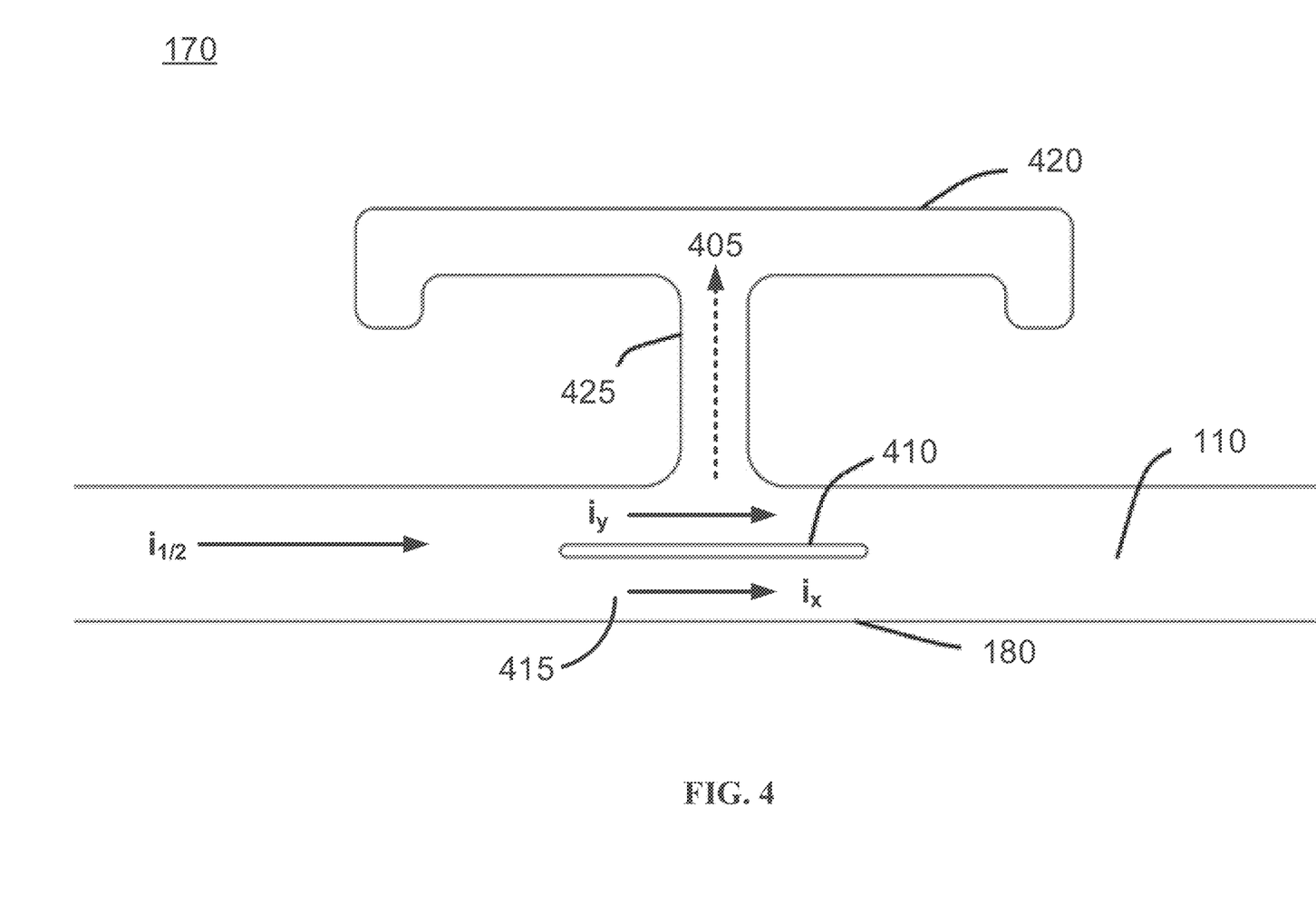
FIG. 4 illustrates a mechanical tab of the microsurgical device shown in FIG. 1A, according to one embodiment.

FIG. 4 illustrates a mechanical tab 170 that couples the cutting element 110 to the suction cup 105. In other designs, the mass of a mechanical tab can create a cold spot in the cutting element 110 underneath the tab because electrical current flowing past below the tab will generate heat in the metal, but the mechanical tab is not heated. Therefore, the tab stays cold and absorbs heat from the cutting element 110 by thermal conduction 405. Cold spots can result in the cutting element immediately below a mechanical tab and giving rise to non-uniform tissue cutting and tissue tags. This problem is accentuated if electrical current is delivered as sequential pulses of energy to the cutting element 110 because the cold tab acts as a heat sink and takes heat away from the bottom of the cutting element 110 via thermal conduction 405 in between pulses if slot 410 is not there to block thermal conduction.

The design of the mechanical tab 170 shown prevents cold spots from forming in the cutting element 110 through the implementation of a mechanical tab slot 410 disposed horizontally along the cutting element 110. The mechanical tab slot 410 allows electrical current $i_x$ to flow horizontally around the bottom half of the cutting element 110, but prevents vertical thermal conduction 405 from the bottom beam 415 to the cold mechanical tab 170 and minimizes the amount of electrical current $i_y$ flowing through the top half of the cutting element. As a result, the cold mechanical tab 170 does not take heat away from the bottom of 110, and a uniform temperature at the inner corner edge 180 of the cutting element 110 is maintained.

The shape of the mechanical tab 170 may vary. The mechanical tab 170 shown includes a horizontal beam 420 and vertical beam 425 that together form a T-shape. The vertical beam 425 of the mechanical tab 170 is connected to the cutting element 110. In other embodiments, the mechanical tab 170 may form a closed circular loop, a closed elliptical loop, a partially open circular loop, a partially open elliptical loop, etc.; the edges of the horizontal beam 420 may extend downward, or the like. In some embodiments, the mechanical tab 170 and the cutting element 110 are continuous and/or made out of the same material.

FIG. 5 illustrates an example embodiment of an anchor tab 175 of the microsurgical device 100 shown in FIG. 1A. In use, an anchor thread 155 may be looped around the anchor tab 175 to hold the cutting element 110 back while the other end of the cutting element 110 is stretched forward by a rigid extender 150. The stretched cutting element 110 may then be inserted through an incision. In some embodiments, the anchor tab 175 and the cutting element 110 are continuous and/or made out of the same material.

The anchor tab 175 includes a bent portion 505 that forms a space 510 around which the anchor thread 155 may be looped. In the embodiment shown, the cutting element 110 includes an anchor tab slot 515 under the anchor tab 175. As with the mechanical tab 170, the mass of the anchor tab 175 may cause a cold spot in the cutting element 110 underneath the anchor tab 175. The anchor tab slot 515 allows the electrical current to flow horizontally around the cutting element 110, but prevents vertical thermal conduction from the bottom beam 520 to the cold anchor tab 175. The anchor tab slot 515 also prevents thermal propagation in between pulses into the anchor tab 175. As a result, a uniform temperature at the inner corner edge 180 of the cutting element 110 is maintained during tissue cutting.

The size and geometry of the anchor tab slot 515 may vary. In some embodiments, the anchor tab slot 515 is longer than the slots under the other tabs. For example, the anchor tab slot 515 may be a predetermined length longer than the mechanical tab slot 410. Additionally, in some embodiments, there is a reduction in current carrying cross-section to provide one or more hot spots 525 next to the anchor tab 175. For example, in the anchor tab 175 shown, the cross-section of the cutting element 110 adjacent to the anchor tab 175 is reduced to create local hot spots 525 on either side of the anchor tab 175. Hot spots 525 may offset the cooling effects of the anchor tab 175 on the cutting element 110.

In some embodiments, the edges 530 of the anchor tabs that contact the anchor thread 155 are smoothed to reduce the risk of cutting the anchor thread 155 during use. For example, the edges 530 may be smoothed by lapping the edges 530 with a thread and 1-micron diamond lapping paste. In some embodiments, the device 100 includes an additional anchor tab adjacent to anchor tab 175. In these embodiments, the anchor thread 155 is looped around both the anchor tab 175 and the additional anchor tab. The additional anchor tab may be a mirror image of the anchor tab 175. Alternatively, the specifications of the additional anchor tab may differ from the anchor tab 175.

Figure 6:
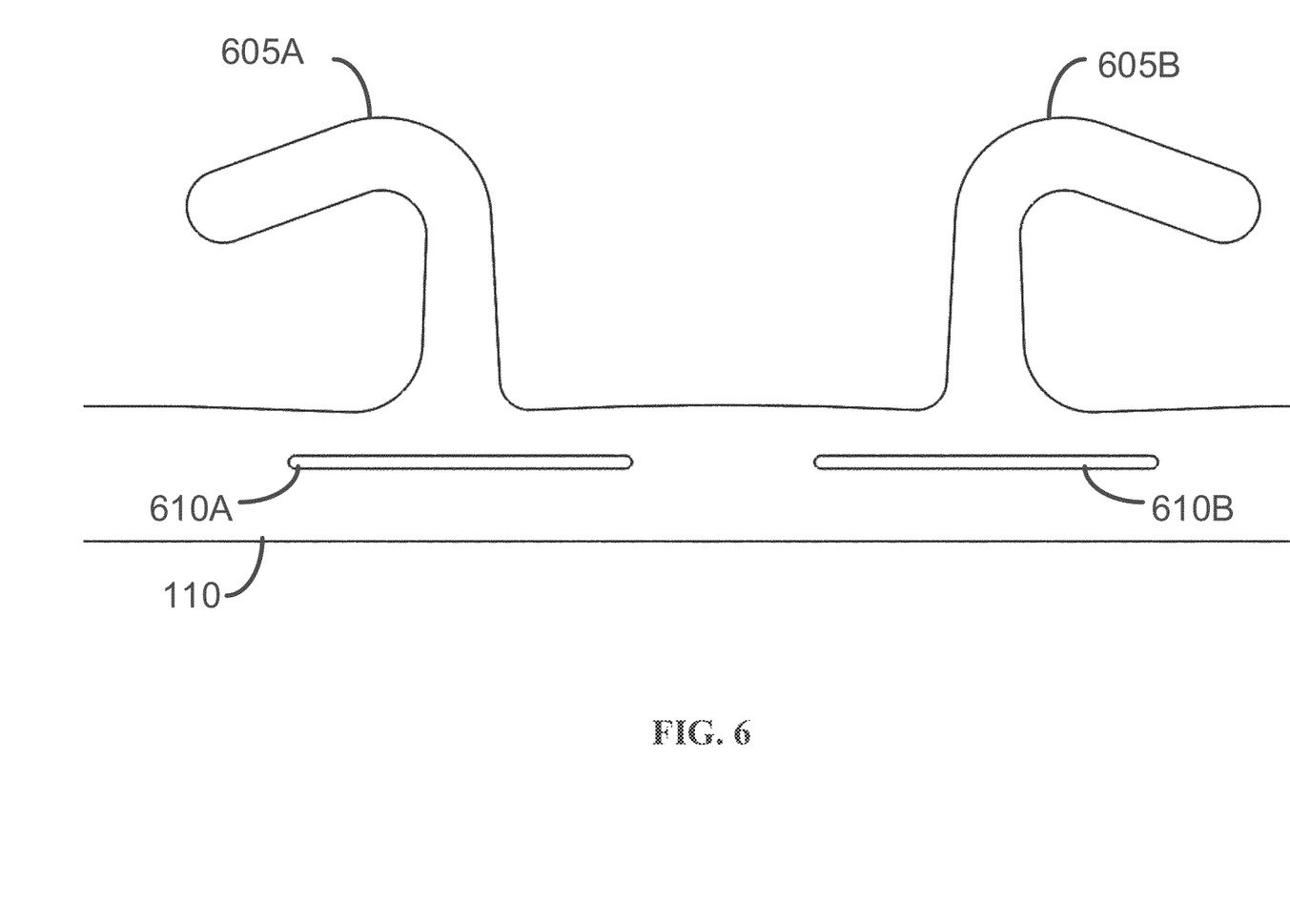
FIG. 6 illustrates a variation of anchor tabs of a microsurgical device, according to one embodiment.

FIG. 6 illustrates a variation of anchor tabs 605A, 605B of a microsurgical device. The anchor tabs 605A, 605B protrude from a microsurgical device with the same or similar functionality to the device 100 described with reference to FIG. 1A. An anchor thread 155 may be looped around the anchor tabs 605A, 605B to hold the cutting element 110 back while the other end of the cutting element 110 is stretched forward by a rigid extender 150.

The specifications, such as the width, height, curvature, etc., of each of the anchor tabs 605A, 605B may be modified. For example, the width of the anchor tabs 605A, 605B may be reduced to reduce the mass of the anchor tabs 605A, 605B. The anchor tabs 605A, 605B shown are mirror images of each other. In other embodiments, the specifications of each anchor tab may differ from each other based on the procedure, tissue shape, and the like. Alternatively, or additionally, a device may include greater or fewer anchor tabs, such as one anchor tab, three anchor tabs, or the like.

A slot, e.g., slots 610A, 610B, is disposed along the cutting element 110 under each of the anchor tabs. The slots 610A, 610B include the same or similar functionality to the anchor tab slot 515 described with reference to FIG. 5. The length of the slots 610A, 610B may be longer, shorter, or of the same length as other slots disposed along the cutting element 110. The base of the anchor tabs may be filleted to reduce mechanical stress. In addition, the cross-section of the cutting element 110 adjacent to either slot 610A, 610B may be reduced to locally increase the current density of the cutting element 110.

Additional Configuration Information

The foregoing description of the embodiments of the disclosure has been presented for the purpose of illustration; it is not intended to be exhaustive or to limit the disclosure to the precise forms disclosed. Persons skilled in the relevant art can appreciate that many modifications and variations are possible in light of the above disclosure.

The language used in the specification has been principally selected for readability and instructional purposes, and it may not have been selected to delineate or circumscribe the inventive subject matter. It is therefore intended that the scope of the disclosure be limited not by this detailed description, but rather by any claims that issue on an application based hereon. Accordingly, the disclosure of the embodiments is intended to be illustrative, but not limiting, of the scope of the disclosure, which is set forth in the following claims.

What is claimed is:

1. A device comprising:
   a suction cup;
   a cutting element;
   one or more electrical leads configured to provide an electrical discharge to the cutting element;
   one or more wire tabs protruding from the cutting element, each of the one or more wire tabs configured to conductively couple an electrical lead of the one or more electrical leads to the cutting element, each wire tab of the one or more wire tabs including one or more conductive paths and one or more conductive shunt paths conductively separated by one or more slots;
   one or more anchor tabs protruding from the cutting element, each of the one or more anchor tabs associated with a slot horizontally disposed along a circumference of the cutting element and positioned to at least partially separate a respective anchor tab from a bottom portion of the cutting element; and
   one or more mechanical tabs protruding from the cutting element, each of the one or more mechanical tabs adjacent to a slot positioned to at least partially separate a respective anchor tab from a bottom portion of the cutting element and configured to couple the cutting element to an inner surface of the suction cup.

2. The device of claim 1, further comprising an anchor thread coupled to the cutting element via the one or more anchor tabs, the anchor thread configured to compress the cutting element for insertion of the device through an incision.

3. The device of claim 1, further comprising a suction tube configured to provide suction to the suction cup, wherein the one or more electrical leads are disposed within the suction tube.

4. The device of claim 1, further comprising a rigid extender configured to compress the cutting element for insertion of the device through an incision.

5. The device of claim 1, further comprising a controller configured to control one or more electrical discharges to the cutting element via the one or more electrical leads.

6. The device of claim 1, wherein a first width of the cutting element includes a cutout adjacent to each of the one or more anchor tabs, wherein the first width of the cutting element is less wide than a second width of the cutting element.

7. A device comprising:
   a stem;
   a cutting element coupled to a distal end of the stem;
   one or more electrical leads for providing an electrical discharge to the cutting element; and
   one or more wire tabs protruding from the cutting element, each of the one or more wire tabs configured to conductively couple an electrical lead of the one or more electrical leads to the cutting element, each of the one or more wire tabs including one or more conductive paths and one or more conductive shunt paths conductively separated by one or more slots.

8. The device of claim 7, further comprising:
   one or more anchor tabs, each of the one or more anchor tabs associated with a slot horizontally disposed along a circumference of the cutting element and positioned to at least partially separate a respective anchor tab from a bottom portion of the cutting element.

9. The device of claim 8, further comprising an anchor thread coupled to the cutting element via the one or more anchor tabs, the anchor thread configured to compress the cutting element for insertion of the device through an incision.

10. The device of claim 8, wherein a first width of the cutting element includes a cutout adjacent to each of the one or more anchor tabs, wherein the first width of the cutting element is less wide than a second width of the cutting element.

11. The device of claim 7, wherein each of the one or more wire tabs further includes an additional slot disposed within a central conductive path of the wire tab, the additional slot conductively separating portions of the central conductive path.

12. The device of claim 7, wherein the cutting element further includes one or more mechanical tabs protruding from the cutting element, each of the one or more mechanical tabs adjacent to a slot horizontally disposed along a circumference of the cutting element and positioned to at least partially separate a respective mechanical tab from a portion of the cutting element.

13. The device of claim 7, further comprising a suction cup, wherein the cutting element is connected to the suction cup along an inner surface of the suction cup.

14. The device of claim 13, further comprising a suction tube configured to provide suction to the suction cup, wherein the one or more electrical leads are disposed within the suction tube.

15. The device of claim 7, further comprising a rigid extender configured to compress the cutting element for insertion of the device through an incision.

16. The device of claim 7, further comprising a controller configured to control one or more electrical discharges to the cutting element via the one or more electrical leads.

17. A device comprising:
   a stem;
   a cutting element coupled to a distal end of the stem;
   one or more electrical leads for providing an electrical discharge to the cutting element; and
   one or more tabs protruding from the cutting element, each of the one or more tabs associated with one or more slots, and wherein at least one tab is a wire tab configured to conductively couple to an electrical lead of the one or more electrical leads to the cutting element, the wire tab including one or more conductive paths and one or more conductive shunt paths conductively separately by the one or more slots.

18. The device of claim 17, wherein a tab of the one or more tabs is an anchor tab, and wherein a slot of the one or more slots is horizontally disposed along a circumference of the cutting element and positioned to at least partially separate the anchor tab from a portion of the cutting element.

19. The device of claim 17, wherein a tab of the one or more tabs is a mechanical tab, and wherein a slot of the one or more slots is positioned to at least partially separate the mechanical tab from a bottom portion of the cutting element and configured to couple the cutting element to a surface of a suction cup.

* * * * *